(12) United States Patent
Hahm

(10) Patent No.: US 7,063,947 B2
(45) Date of Patent: Jun. 20, 2006

(54) SYSTEM FOR PRODUCING SYNTHETIC PROMOTERS

(75) Inventor: Sung Ho Hahm, Woodstock, MD (US)

(73) Assignee: Promogen, Inc., Gaithersburg, MD (US)

( * ) Notice: Subject to any disclaimer, the term of this patent is extended or adjusted under 35 U.S.C. 154(b) by 75 days.

(21) Appl. No.: 10/907,620

(22) Filed: Apr. 8, 2005

(65) Prior Publication Data

US 2005/0227246 A1 Oct. 13, 2005

Related U.S. Application Data

(60) Provisional application No. 60/560,921, filed on Apr. 8, 2005.

(51) Int. Cl.
*C12Q 1/68* (2006.01)

(52) U.S. Cl. ........................................ 435/6; 435/320.1

(58) Field of Classification Search .................... None
See application file for complete search history.

(56) References Cited

OTHER PUBLICATIONS

Li et al., Nature Biotechnology, vol. 17, 1999, pp. 241-245.*
Bi et al., Journal of Biotechnology, vol. 93, 2002, pp. 231-242.*
Nettelbeck et al., Trends in Genetics, vol. 16, 2000, pp. 174-181.*

* cited by examiner

*Primary Examiner*—James Ketter
(74) *Attorney, Agent, or Firm*—JHK Law; Joseph Hyosuk Kim

(57) ABSTRACT

The present application discloses a method for making and selecting a transcription enhancing combined promoter cassette, which includes constructing a library of randomly combined transcription regulatory elements, which comprise double stranded DNA sequence elements that are recognized by transcription regulators; inserting the combined transcription regulatory elements upstream of a minimum promoter followed by a reporter gene in a vector; inserting the vector into a host cell; and then screening for the cells showing enhanced expression of the reporter gene, and identifying the combined promoter cassette in the cell.

12 Claims, 1 Drawing Sheet

SYSTEM FOR PRODUCING SYNTHETIC PROMOTERS

CROSS-REFERENCE TO RELATED APPLICATIONS

The present application claims the benefit of priority to U.S. Provisional Application No. 60/560,921, filed Apr. 8, 2005, the contents of which are incorporated by reference herein in its entirety.

BACKGROUND OF THE INVENTION

1. Field of the Invention

The present application relates to a system for designing promoters for efficient expression of genes.

2. General Background and State of the Art

Despite early expectations as a promising new technology for the treatment of various diseases, convincing clinical efficacy of gene therapy has not been demonstrated in most of the trials conducted so far. One of the major technical hurdles in clinical gene therapy has been the difficulty of delivering the therapeutic gene into specific target cells and maintaining transgene expression at a sufficiently high level for a desirable amount of time. Although targeting the delivery of therapeutic genes to specific cell types (targeted transduction) will be the most desirable, it represents a major technical obstacle and only limited success has been reported in this field (5, 24, 48). As an alternative approach, scientists have used cell type-specific promoters to restrict expression of transgenes only in target cells (targeted transcription) (18). These promoters are tailored from genes expressed specifically in the same target cells (28, 43, 51, 55). However, these so-called cell-specific promoters are frequently leaky in terms of target cell selectivity, causing transgene expression in non-target cells at variable levels. In most cases, these promoters are not strong enough to mediate transgene expression at or above the level required for realistic therapeutic effects. These facts indicate a need for a more systemic approach for the development of highly efficient cell type-specific promoter systems.

SUMMARY OF THE INVENTION

The invention is directed to the production of synthetic combination of transcription regulatory sequences that can drive gene expression with high efficiency in specific cell types.

In one aspect of the invention, the production may be accomplished by (1) constructing a library of random combination of DNA sequence elements that are recognized by desired transcription regulators; (2) high throughput screening of the library using a cell sorter such as FACS (fluorescence-activated cell sorter) to select a small number of the best performing combinations of DNA sequence elements; and optionally (3) further testing each of the selected combinations for final selection of one or several best performing ones.

In a particular embodiment of the invention, the library may be made by randomly ligating together double stranded DNA oligonucleotides, each of which may contain a DNA sequence element capable of binding a transcription regulator with high affinity.

The DNA sequence elements to be included in the oligonucleotides used in the random ligation reaction may be determined based on different methods, including DNA microarray profiling of transcription factors in the target cells or selectively amplifying high affinity binding sequence elements from a pool of oligonucleotides containing random nucleotides. The DNA sequence elements can also be determined using algorithm-based computer analysis of sequences of genes expressed in the target cells.

In further detail, the randomly combined sequence elements may be cut with a restriction enzyme and cloned in upstream of a reporter gene, which can be without limitation GFP or LacZ, and a library of plasmid DNA or viral vector may be generated. The library can be produced using without limitation retroviral vectors or adenoviral vectors.

The vector DNA containing the library of random sequence combinations cloned upstream of a minimum promoter followed by the reporter gene may be transfected or infected into the target cells and sorted with FACS for the selection of cells expressing high levels of the reporter gene. Sorted cells are then used to recover and amplify the vector DNA containing the desired high performing transcription regulatory element combination.

The vectors recovered and amplified from sorted cells may be inserted into the target cells and selected for the highest performing transcription regulatory element combination again by using FACS. And the same procedure of insertion of the recovered vector DNA to cells, sorting for the highest expressing cells, and recovery of the vector DNA from sorted cells may be repeated several times to refine and obtain a small number of the highest performing ones out of millions of different combinations.

Upon the completion of repeated sorting and selection, recovered DNA vectors may further be screened individually in the target cells to test for their true promoter activity.

As a control, if cell-type specific promoters are desired, the selected vectors containing the transcription regulatory element combinations may also be tested in non-target cells for the purpose of eliminating vectors with substantial promoter activities in non-target cells.

In one aspect of the invention, the invention is directed to a method for the production of synthetic combined promoter cassettes to be used in gene or virus therapy vectors. These synthetic promoters, selected from millions of potential candidates, can drive transgene expression in specific target cells with greatly improved efficiency and selectivity compared with other currently available promoter systems. In one aspect, the system utilizes high throughput assay systems, such as but not limited to DNA microarray and fluorescence-activated cell sorter (FACS), and can be applied to produce synthetic promoters specific for virtually any types of cell in a short period of time. The invention significantly increases the efficacy of currently available gene or virus therapy vector systems which depend on targeted gene transcription. At the same time, it allows rapid introduction of various new gene or virus therapy drug candidates into the market for the treatment of cancer and other diseases.

In a particularly exemplified aspect of the invention, synthetic promoter cassettes capable of targeting gene transcription specifically to neuroblastoma cancer cells are produced. Further in particular, the invention is directed to constructing a library of random combinations of cis-acting sequence elements based on DNA profiling of transcription regulators in target neuroblastoma cells. Millions of different combinations of cis-acting sequence elements may be produced by randomly ligating double-stranded oligonucleotides containing various cis-acting sequence elements for the binding of transcription regulators specifically expressed in neuroblastoma cells. Cis-acting sequence elements to be included in the random ligation reaction are determined based on previously performed DNA microarray expression profiling of transcription regulators and related proteins in the target neuroblastoma cells. The randomly ligated sequence element combinations are cloned upstream of a minimum promoter followed by a reporter gene such as lacZ or GFP.

In another particular aspect of the invention, the invention is directed to pre-screening the library using a FACS-based directed-evolution protocol. The plasmid library may be screened to select a small number (approximately 90) of the best performing combinations in target neuroblastoma cells, which are chosen to undergo more extensive screening procedure to identify the highest performing combination of sequence elements specific for a given target cell. This in vitro evolution method partially depends on the ability of high throughput cell sorting technology such as FACS to sort cells expressing the reporter gene product such as β-galactosidase after transfecting or infecting them with the library of the reporter gene vector.

In addition, the invention is directed to screening the pre-selected cis-acting sequence combinations individually in 96-well transient transfection/infection assays both in target and non-target cells. The performance of each of the approximately 90 pre-selected combined promoter cassettes are evaluated, and about 3–5 best performing combination of sequence elements are selected in terms of their strength in promoter activity in target cells and the absence of activity in non-target cells. A collection of non-target cell types, including neuronal precursor cells and neuronal cells, are used for the screening to make sure that the selected promoter cassettes containing the combination of sequence elements are truly selective for the target neuroblastoma cells.

The selected neuroblastoma-specific promoter cassette may be cloned in vectors such as without limitation retroviral and adenoviral vectors for additional testing of their activities in native chromatin or chromatin-like environments, both in target and non-target cells. The single best-performing cassette is used in various vector systems to be developed into neuroblastoma cancer gene therapy or oncolytic virus therapy drug candidates following animal trials.

The present invention is directed to a method for making and selecting a combined promoter cassette comprising: (i) constructing a library of randomly combined transcription regulatory elements comprising multiple sequence elements that are recognized by different transcription regulators; (ii) inserting the combined transcription regulatory elements upstream of a minimum promoter followed by a reporter gene in a vector; and (iii) screening for the highest level of expression of the reporter gene in a specific cell, which sequence upstream of the reporter gene comprises the selected promoter cassette.

The library of randomly combined transcription regulatory elements comprising multiple DNA sequence elements that are recognized by different transcription regulators may be made by mixing together double stranded oligonucleotides containing different DNA sequence elements under ligation reaction conditions. Further, the ends of the oligonucleotides may contain flanking nucleotides which may be blunted or cut with restriction endonucleases to produce protruding ends prior to undergoing the ligation reaction. In one aspect, the reporter gene may be lacZ and the reporter gene expression may be screened by fluorescence-activated cell sorter (FACS).

Further, in the above method, the DNA sequence elements that are recognized by cell type-specific transcription regulators may be obtained by DNA microarray profiling of the transcription regulators expressed in the specific target cells.

In the methods described above, the specific cell type may be cancer-carcinoma, sarcoma, melanoma, and in particular, neuroblastoma.

In another aspect, the invention is directed to a vector comprising the combined transcription regulatory element described above. The vector may be a plasmid, virus, transiently expressed, or capable of being integrated into the host cell genome.

The invention also includes host cells of prokaryotic or eukaryotic origin, such as *E coli* plant, insect, mammalian, and human.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
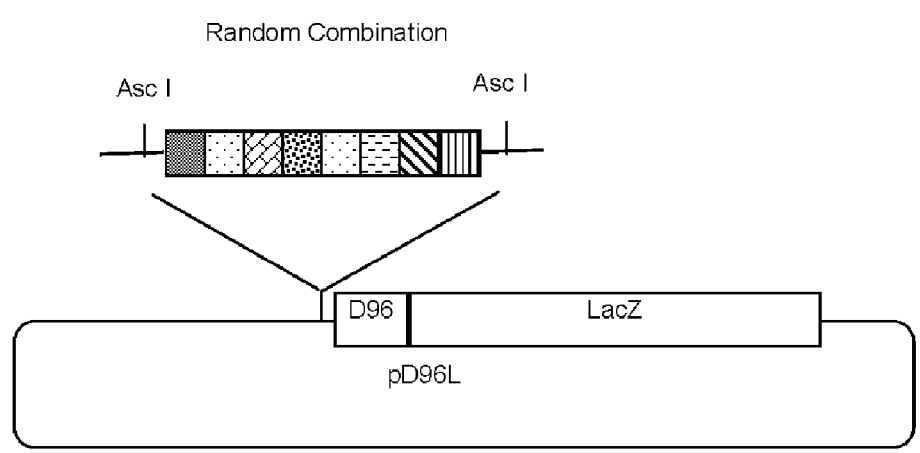
FIG. 1 shows a vector system in which the transcription regulatory elements are randomly ligated to each other and cloned upstream of a minimum promoter (D 96) followed by the reporter gene (LacZ).

In the present application, "a" and "an" are used to refer to both single and a plurality of objects.

As used herein, "transcription regulatory element" refers to a nucleotide sequence that is recognized by a transcription regulator, and is synonymous with "cis-acting sequence" or "cis-acting sequence element" or "cis-acting region", and sometimes expressed as "sequence element".

As used herein, "combined transcription regulatory element" refers to a double stranded DNA molecule that includes more than one transcription regulatory element. The combined transcription regulatory element may be created by ligating various double stranded transcription regulatory elements in a random fashion. Optionally, the combined sequence element may contain a spacer region and the length of the spacer nucleotides may be controlled by subjecting the double stranded DNA molecules to time-course exonuclease digestion before using them in random ligation reactions.

As used herein, "oligonucleotide" refers to a sequence that functionally includes a cis acting region and perhaps up to about 25 or less extraneous nucleotides. Therefore, the number of nucleotides that are encompassed by the term "oligonucleotide" cannot be fixed, and therefore is not limited to any particular number of nucleotides.

As used herein, "promoter cassette" or "synthetic promoter cassette" refers to DNA segment that contains components for an efficient transcription of a gene, and may include one or more transcription regulatory element, a minimum promoter region, sequences from 5'-untranslated region or introns.

As used herein, "minimum promoter region" or "minimum promoter" refers to a short DNA segment which is inactive by itself, but can mediate strong transcription when combined with other transcription regulatory elements.

Minimum promoter sequence can be derived from various different sources, including prokaryotic and eukaryotic genes. Examples of this are dopamine beta-hydroxylase gene minimum promoter and cytomegalovirus (CMV) immediate early gene minimum promoter.

As used herein, "combined promoter cassette" or "synthetic combined promoter cassette" refers to promoter cassettes containing combined transcription regulatory elements.

As used herein, a "transcription regulator" refers to any factor including proteins that bind to the cis-acting region and regulate either positively or negatively the expression of the gene. Transcription factors or repressors or co-activators or co-repressors are all included.

Transcription Regulator Expression Profiling

Transcription regulator expression profiling may be carried out by a variety of methods. Methods of determining which transcription factors are present in a cell type of interest and which cis-regions are the binding sites for the transcription factors or repressors may be carried out using a variety of methods. In one aspect of the invention, DNA microarray-based transcription factor expression profiling may be used to design the synthetic promoter cassettes. Eukaryotic gene transcription is an intricate biochemical process involving combinatorial effects from multiple protein regulators including transcription activators, repressors, co-activators and co-repressors (7, 15, 29, 35). Therefore, knowing the exact profile of these proteins available in different cell types greatly helps to understand how different combinations of these proteins mediate gene transcription in these cells.

In the present invention, expression profiling was performed in three neuroblastoma cell types using a commercially available DNA microarray chip spotted with oligonucleotides for 1500 different genes encoding transcription regulators and other proteins directly or indirectly involved in gene transcription. The results show various cell type-specific expressed transcription regulators. The pattern of expression of several developmentally regulated transcription regulators matches closely with previous observations reported in the literature. This shows that the microarray assay is sensitive enough to detect transcripts expressed at relatively low levels. Based on the data from these microarray assays, transcription factors specifically expressed in neuroblastoma cells are determined.

Cis-acting sequence elements of these neuroblastoma-specific transcription regulators are then determined using published reports and other sources that list the cis-acting sequences for the identified transcription regulators, and they are used for the construction of synthetic promoter cassettes capable of targeting gene transcription selectively in these target cells.

Expression profiling for transcription regulators and related proteins is carried out in many different cell types, and a database is generated. This database (named TREP database for Transcription Regulator Expression Profile) contains detailed information about the differences between cell types in the level of expression of various tissue-specific or constitutively expressed transcription regulators and related proteins. Generalized patterns of expression profile can be deduced for different groups of cells. The database thus facilitates our understanding of how different combinations of these proteins are used for cell type-specific gene expression during the normal course of development and in neoplastic transformation. At the same time, the TREP database becomes a tool for the design and synthesis of promoter cassettes to be used for target cell-specific and/or pharmacologically-inducible expression of transgenes.

In situations where the cis-acting sequences for an identified transcription regulator is not available, such a DNA sequence element can be obtained experimentally. For instance, a population of oligonucleotides containing random nucleotide sequences can be mixed with the purified transcription regulator under binding reaction conditions, and binding to any of the oligonucleotides is assayed using conventional methods. The bound oligonucleotide may be sequenced to determine the nucleotide sequence of the cis-acting region.

Construction Of A Library Of Random Sequence Element Combinations

Once the expression profile of the transcription regulators and related proteins is known for a given cell type, synthetic combined transcription regulatory elements can be made by combining cis-acting sequence elements for the transcription regulators specifically expressed in the target cells. In order to increase promoter strength, cis-acting sequences for several ubiquitously expressed transcription factors can also be included in the construction. A maximum transcription efficiency is achieved from cis-acting sequences included in the combined promoter cassette for ubiquitously expressed transcription factors in the target cells. On the other hand, target cell specificity is determined from the cis-acting sequences included in the cassette for the binding of transcription factors specifically expressed in the target cells. The availability of co-activators of these transcription factors in the target cells is also considered when selecting for the cis-acting sequences.

When assembled properly, these combined transcription regulatory elements bind multiple transcription regulators expressed in the particular target cells and efficiently drive transgene expression. The same combined transcription regulatory elements are inactive in non-target cells due to the lack of particular transcription regulators required for binding to the sequence elements.

The combined transcription regulatory elements may also include sequence elements for the binding of transcription repressors expressed only in non-target cells, further enhancing target cell specificity of transgene expression. The presence of the cis-acting sequence element in the promoter cassette for the binding of the repressor protein will cause an effective inhibition of transcription in non-target cells expressing high levels of the repressor protein. On the other hand, it will have no effect in target cells as they do not express the same repressor protein. Thus, the combinatorial nature of gene transcription is most effectively utilized, by knowing the exact profile of transcription regulators and co-regulators expressed in the target versus non-target cells.

Efficient transcription of a gene requires combinatorial interactions of transcription factors and cofactors assembled on the promoter/enhancer region of a particular gene (15, 16, 29). Transcription factors bind to cis-acting sequence elements in the promoter/enhancer region of a gene arranged in a specific order with particular space constrictions. The most efficient transcription from a synthetic gene promoter cassette is achieved only when different transcription factor binding sequence elements are arranged in a specific order and with proper spacing between them. In theory, there are more than 3 million different possible arrangements for 10 different cis-acting sequence elements, assuming each element is used only once for the combinations having the length of 10 sequence elements. Thus, if performed using conventional methods, a tremendous amount of time would be required to assemble and test all these possible combinations to determine the best arrangement of sequence elements for multiple transcription factors.

This limitation may be overcome by employing the inventive method, which includes (1) employing a random ligation reaction to produce a library of cis-acting sequence element combinations; pre-screening the library to select approximately 90 best-performing combinations in a directed-evolution method using a flow cytometer (FACS) in target cells; and screening the pre-selected or pre-screened sequence element combinations both in target and non-target cells in transient transfection assays such as in 96 well plates for the selection of about 3–5 final candidates.

During the random ligation reaction, millions of different combinations of sequence elements are produced with a high degree of likelihood of containing combinations with an optimum arrangement of sequence elements for the strong and selective transcriptional activity in the target cells.

Pre-Screening The Library Using FACS-Based Directed Evolution

One aspect of the invention is directed to a pre-screening method, which uses an adaptation of the FACS-based directed-evolution protocol as described in Huang et al (20), the contents of which are incorporated by reference herein in its entirety, especially with respect to the protocol for using FACS.

Huang et al (20) report a FACS-based method applied to selecting functional enhancer/promoter sites for the muscle-specific transcription factor MyoD from random DNA sequences. Oligonucleotides with random nucleotides embedded in a muscle-specific minimum promoter are cloned upstream of the β-galactosidase gene. The resulting plasmid library is co-transfected with a MyoD expression vector into NIH 3T3 cells. Cells expressing high levels of β-galactosidase are selected by FACS and the majority of cells expressing low to intermediate levels of the reporter gene are eliminated. Sorted cells (approximately 5% of the original population) thus contain plasmids with high levels of transcriptional activity mediated by the binding of MyoD to high affinity sequence element. Plasmids are extracted from these selected cells by the Hirt protocol (19), amplified, and used again for transfecting cells and sorting by FACS, and the same procedure of DNA extraction and amplification, transfection, and sorting is repeated. After three rounds of such sorting and amplification, the cell population is highly enriched for cells transfected with plasmids capable of mediating the highest level of reporter gene expression. The selection pressure in this directed-evolution protocol is the efficiency of the binding of MyoD to random sequences for the activation of β-galactosidase reporter gene. This approach is both powerful and rapid because FACS can detect as few as 5 β-Gal molecules per cell (44) and it can sort approximately one million cells per hour. The procedure for fluorescence-activated cell analysis and sorting of viable mammalian cells based on β-galactosidase activity after transfecting with E coli LacZ reporter gene is well established (12, 44).

In the present invention, the basic concept of FACS-based selection protocol by Huang et al (20) has been modified so that reporter gene expression is mediated by random combinations of multiple sequence elements. In this case, combinatorial input from multiple transcription factors binding to randomly combined sequence elements, rather than the binding of a single factor to random nucleotides, determines the efficiency of reporter gene expression. One distinguishing feature of this approach is in selecting sequence combinations in real time in target cells in the presence of all the relevant regulators and co-regulators. This protocol is used for prescreening the library of cis-acting sequence element combinations for the purpose of rapidly eliminating the majority of combinations with low-to-intermediate transcriptional capability in target cells. Approximately 90 best performing sequence combinations are selected making them manageable for a more intensive screening by transfecting/infecting in 96-well formats both in target cells and non-target cells. Each cell type is plated in a 96-well plate and transfected/infected with the 90 selected clones plus positive and negative control vectors. Transient transfection/infection screening in target cells allows the approximately 90 selected clones to be ranked in terms of their strength in promoter activity. In addition, screening of these clones in non-target cells may be used, if cell type-specific promoter cassettes are desired, to eliminate all the leaky clones with detectable activity in these non-target cells. Many different non-target cell types (both primary cells and cell lines) are tested in the screening to make sure that the selected sequence combinations are truly selective for target cells. About three to five best performing combined promoter cassettes may be selected and further tested after cloning in viral vectors.

The inventive methods of making the synthetic combined promoter cassettes may be applied to virtually any type of cell, preferably cancer cell. According to a web-based database available to the public and provided by the Journal of Gene Medicine (updated Jan. 31, 2004) for the worldwide gene therapy clinical trials, there are 918 gene therapy clinical trials underway worldwide. The most frequently treated type of disease in the clinical gene therapy trials is cancer, comprising 66% (608 trials). Approximately 190 of these trials use either suicide genes or tumor suppressor genes. These trials depend on the ability of the therapeutic gene products to kill cancer cells effectively and selectively without an effect on normal cells of the patient. The inventive method may be used for the production of synthetic promoters specifically designed for the requirements of each of these cancer gene therapy trials resulting in improved efficacy.

Neuroblastoma Cell-Specific Transcription Regulators

Although any cell type can be used to practice the invention, neuroblastoma is exemplified herein as the target cell. Thus, in one aspect of the invention, neuroblastoma cancer cell-specific synthetic combined promoter cassettes are produced. Neuroblastoma is one of the most common solid tumors of early childhood originating in the adrenal medulla or other sites of sympathetic nervous tissue. There are approximately 650 new cases of neuroblastoma each year. It is characterized by a diversity of clinical behavior ranging from spontaneous regression to rapid tumor progression and death (54). Although low-stage tumors are often successfully treated by surgical resection, high-stage malignant neuroblastoma is extremely aggressive and fatal in older children even after intensive multimodal therapies (42). Therefore, there is an urgent need for advanced treatment strategies such as gene therapy or oncolytic virus therapy for the high-stage neuroblastoma patients.

Multipotent neural crest cells differentiate into various neural and neuroendocrine cell types during the normal course of embryonic and post-embryonic development. Consequently, neuroblastoma tumors derived from multipotent neural crest cells contain multiple cell phenotypes. Many cell lines have been established from neuroblastoma primary tumors or from bone marrow metastases, and have been widely used in different fields of molecular and cellular studies. Long-term studies have shown the presence of three different cell types in neuroblastoma cell lines: I-type stem cells, N-type neuroblastic-neuroendocrine precursors, and S-type Schwannian-melanoblastic precursors (49). I-type stem cells are significantly more malignant than either N- or S-type cells. A comprehensive genetic and histopathologic study revealed three similar types of cells in human neuroblastoma tumors (33). Presumptive I-type stem cells are present in tumors of all stage. Tumors contain N-type neuroblastic cells in various stages of differentiation. Stromal cells contain tumor-derived S-type cells and normal cells. Three such different types of neuroblastoma cell lines are used as target cells for the purpose of designing neuroblastoma cell-specific synthetic combined promoter cassettes: I-type: SK-N-BE(2)-C cells; N-type: SH-SY5Y cells; S-type: SH-EP1 cells.

Synthesis of the combined promoter cassettes capable of mediating gene expression efficiently in these three cell types is carried out. The combined promoter cassettes produced based on selection in these cell lines have a high likelihood of performing in the same way in vivo in animal trials and in clinical trials.

The 3–5 neuroblastoma-specific combined promoter cassettes selected from transient transfection assays are further tested after placing them in viral expression vectors. Eukaryotic genome is packaged into a complex chromatin structure, and it has been reported that remodeling of chromatin structure by proteins, such as histone acetyltransferases and ATP-dependent chromatin remodeling factors, is required for the facilitation of transcription (13, 53). Retrovirus vectors are stably integrated into the host genome and adenovirus genome complex with viral basic proteins in a nucleosome-like structure at least during the early stages of infection (45). Thus, recombinant retrovirus and adenovirus LacZ expression vectors equipped with synthetic combined promoter cassettes selected in in vitro studies are tested again in animal studies for their specificity and efficiency of expression in target and non-target cells. One best performing synthetic combined promoter cassette is chosen and is further developed into a gene or virus therapy drug candidate for clinical trials in appropriate vectors. Thus for instance, it can be used for neuroblastoma cancer cell-specific expression of a suicidal or cytotoxic gene in cancer gene therapy trials or in vectors for neuroblastoma-specific oncolytic virus therapy trials.

In another aspect of the invention, the production of synthetic combined promoter cassettes targeting different cancer types may be optimized. The protocol is optimized so that the FACS-based pre-screening procedure may be performed using primary cells. This allows the application of the technology in cancer types without any appropriate cell line established for performing the screening procedure. Primary cancer cells can be prepared from fresh tissue samples obtained through the Cooperative Human Tissue Network of the National Cancer Institute. A successful application of FACS-based procedure for pre-screening the library of sequence combinations greatly depend on the efficiency of transfection of target cells. Generally, lipid- or calcium phosphate-based transfection methods achieve less than 25% of transfection efficiency in primary cells. In order to overcome this limitation, lentivirus-based and/or electroporation-based gene transfer methods are tested to achieve higher level of transfection efficiency. The advantage of using lentivirus system is its ability to transduce cells in quiescent or growth arrested stage. A promoterless lentivirus vector system is commercially available (Invitrogen, Carlsbad, Calif.). Using this system, a library of lentivirus vectors containing different combinations of sequence elements driving β-galactosidase gene expression can be produced and packaged for transduction of primary cells in a relatively short period of time. Electroporation is another method for transfecting primary cells with relatively high efficiency.

Another method of the invention for optimizing and streamlining the vector technology is enlarging the Transcription Regulator Expression Profile (TREP) database by collecting data from a variety of cell types. When the database is built from a sufficiently large number of cell types, generalized patterns of transcription regulator expression profile can be deduced for each particular group of cells, which help the designing part of the proposed protocol to be done in a more predictable manner. Other relevant information is also included in the database, such as the nucleotide sequences of the approximately 90 pre-selected random combined promoter cassettes from each FACS-based selection experiment and their promoter activities in transient transfection assays both in target and non-target cells. As the technology is applied for synthesizing combined promoter cassettes targeting various cancer types, the database accumulates information about the behavior of different combinations or groups of transcription factors in specific cell types. In the long-run, the database allows the designing of synthetic promoter cassettes to be done more accurately and effectively by allowing the designer to predict the outcome of certain combinations of transcription factors even before performing the assay.

The present invention is not to be limited in scope by the specific embodiments described herein. Indeed, various modifications of the invention in addition to those described herein will become apparent to those skilled in the art from the foregoing description and accompanying FIGURE. Such modifications are intended to fall within the scope of the appended claims. The following examples are offered by way of illustration of the present invention, and not by way of limitation.

EXAMPLES

Example 1

Microarray Expression Profiling of Transcription Regulators and Related Proteins in Neuroblastoma Cells Example 1.1

Experimental Procedures

Example 1.1.1

Cell Culture and Total RNA Isolation

SH-EP1, SH-SY5Y, and SK-N-BE(2)-C neuroblastoma cells were cultured in D-10 medium: Dulbecco's modified Eagle's medium with 4.5 g of glucose per liter, containing 10% fetal bovine serum (heat inactivated) supplemented with glutamine (0.03%), penicillin (100 units/ml), and streptomycin (100 µg/ml). Cells were maintained in a humidified 95% air, 5% carbon dioxide atmosphere in a 37° C. incubator. Total RNA was extracted from cells grown to 80–85% confluence in T150 tissue culture flasks, using the RNeasy midi kit (Qiagen) following the manufacturer's protocol, and stored at −80° C. in aliquots.

Example 1.1.2

Microarray Assay

The expression profiles of transcription factors and related proteins were obtained from SH-EP1, SH-SY5Y, and SK-N-BE(2)-C neuroblastoma cells using the Proteomic Regulatory Oligonucleotides Microarray (PROM) chips produced by Geneka Biotechnology, Inc. The chip contains 35–45 base pair oligonucleotides spotted in duplicates from 1500 genes for transcription factors, cofactors, DNA-binding proteins, and other proteins involved in gene transcription. cDNA synthesis and labeling with fluorescence dyes, microarray hybridization, microarray scanning, and data analysis were performed at Geneka Biotechnology, Inc. Briefly, assays were performed by co-hybridizing each of the neuroblastoma cell cDNA with the HeLa cell cDNA labeled using different fluorescent tags (Cy5 vs. Cy3), which allow the comparison of the relative level of expression of each of the 1500 genes among the three different neuroblastoma cell lines. The relative level of expression of each gene from neuroblastoma cells is shown as a ratio against the level of expression in HeLa cells. In addition, each oligonucleotide chip contains probes for the Agamous(plant) gene as an external control, and for the 18S rRNA, β-actin and GAPDH genes as internal controls, which are used to normalize the signals. Each neuroblastoma cell line was screened in duplicate slides, such that the first slide was hybridized with Cy5-labelled neuroblastoma cDNA against Cy3-labeled HeLa cDNA, and the second slide with Cy3-labeled neuroblastoma cDNA against Cy5-labeled HeLa cDNA.

Example 1.2

Results and Discussion

The results from PROM microarray assay show various genes differentially up- or down-regulated in these three different neuroblastoma cell types. Some of the interesting observations include the detection of cell type-specific expression of NeuroD gene transcripts in SH-EP1 cells and Phox2b gene transcripts in SH-SY5Y and SK-N-BE(2)-C cells, respectively. NeuroD is a member of the basic helix-loop-helix transcription factor family and plays an important role in the differentiation of neuronal precursor cells (1). During embryonic development of the peripheral nervous system, NeuroD mRNA is expressed transiently in postmitotic neuronal precursor cells (34). On the other hand, Phox2b is a homeodomain transcription factor that controls the generation and survival of distinct neuronal types (4, 10). Phox2b and Phox2a are co-expressed in all central and peripheral neurons expressing noradrenergic biosynthetic enzyme dopamine β-hydroxylase (DBH) (46). Kim et al., (27) have shown that DBH gene has at least 2 cis-acting sequences for these homeodomain proteins in its 5' promoter region. Because Pho2b expression is detected only in SH-SY5Y and SK-N-BE(2)-C cells that are noradrenergic but not in the cholinergic SH-EP1 cells in the assay, it confirms what is known from the literature. Other examples of cell-specifically up-regulated transcription factors and cofactors include: NPAS1 (neuronal basic helix-loop-helix-PAS family member) and TBX21 (T-box protein) in SH-EP1 cells, ATF-3, C/EBP-alpha, NFkB, and PIAS3 (protein inhibitor of activated STAT3) in SH-SY5Y cells, and CBP (CREB binding protein), HTLF (T-cell leukemia virus enhancer factor), N-Myc and Oct-1 In SK-N-BE(2)C cells. The ability of the PROM microarray assay to detect these examples of developmentally or cell type-specifically regulated gene transcripts suggests that the assay is sufficiently sensitive to detect transcripts expressed at a relatively low level. If, however, a transcription factor gene expressed at a low level is chosen for the synthetic promoter construction, either Northern blot analyses or gel mobility shift analyses may be performed to confirm the microarray results.

The PROM microarray data shows members of the Sox, Hox, Pbx, Pax, Egr, and nuclear hormone receptor families to be specifically expressed in all three neuroblastoma cell types. Extensive studies of available literature reveal that these transcription factors are involved in embryonic development and cell differentiation in one way or another. Intricate combinatorial interactions of these transcription factors, as well as other ubiquitously expressed transcription regulators and co-regulators, trigger expression of specific genes required for the determination of the fate of cells during neural crest development (31, 52, 57). Some of the co-regulators up-regulated in neuroblastoma cells include SNW1, N—CoR, NCOA3, and HDAC6. In addition, two closely related transcription repressors known to be involved in suppressing c-myc expression were down-regulated in all three neuroblastoma cells.

Cis-acting sequence elements for 10 different transcription factors, chosen from the above neuroblastoma cell-specific transcription factors and members of the Oct, CREB, AP-1 and STAT families for constitutively expressed transcription factors, are used in random ligation reactions. Neuroblastoma cell-specific down-regulated repressor elements may also be included in the random cassette construction. As this particular transcription repressor is not expressed in neuroblastoma cells, the sequence element for the binding of this repressor protein included in the random combinations will have no effect on the level of transcription driven by the promoter combinations in neuroblastoma cells. On the other hand, the same repressor element will work as an inhibitor of transcription in non-target cells expressing high levels of the repressor protein.

Sequence elements to be included in the library construction are determined after considering the potential of each corresponding transcription factor in playing a role by closely cooperating with other participating members for efficient gene transcription in neuroblastoma cells. Sp-1 binding sequence elements are also included in the reaction because Sp-1 is known to act in synergy with other transcription factors, and Sp-1 binding sites are essential for the protection of the CpG islands from methylation (3, 40, 41).

Expression profiles of transcription regulators and co-regulators were obtained from three relevant target neuroblastoma cell types. The data provide more meaningful and accurate information for the design and construction of cancer cell-specific promoter cassettes, compared to a case where expression profile is obtained from single target cell type. However, actual determination of cis-acting sequence elements for transcription factors or repressors to be included in the random ligation reaction in the project, required careful studies of available literatures. The studies were conducted to determine the best candidate sequence elements that, when combined, perform cooperative interactions with other components for an efficient and selective transcription in target cells.

Example 2

Construction of a Library of Random Combinations of Sequence Elements Based on DNA Microarray Profiling of Transcription Factors Complementary oligonucleotides containing the conserved cis-acting sequences for the binding of each of the selected transcription factors are synthesized and annealed. A random ligation reaction is carried out using a mixture of annealed oligonucleotides (36). The resulting random extensions of multiple cis-acting sequences are subcloned upstream of the human dopamine β-hydroxylase (DBH) gene minimal promoter followed by the LacZ reporter gene. The DBH minimum promoter (−45 to +51 from transcription start site) containing TATA box was chosen because DBH is specifically expressed in neural crest-derived cells including neuroblastoma cell lines (27, 59). The DBH minimum promoter was shown to be inactive by itself, but mediates strong cell-specific transcription when combined with other sequence elements (21).

Cis-acting sequence containing oligonucleotides to be used in the random ligation reaction are designed carefully, considering the importance of the spacing between cis-acting sequences or their distance from the transcription start site. In order to increase the efficiency of transcriptional activation, sequences flanking the core motif of each regulatory element are taken from conserved genes expressed specifically in neuroblastoma cells. These flanking sequences are determined such that the core regulatory elements would appear on the same face of the DNA double helix when reassembled. The Protein Data Bank contains more than 250 structures of protein-DNA complex (2). Combined with molecular and biochemical studies, these structures have illustrated various strategies by which proteins bind selectively to particular DNA sequences. Information from all available sources is used to determine the precise architecture of the oligonucleotides to be added in the synthetic promoter cassettes. In certain cases, double stranded oligonucleotides containing individual cis-acting sequence elements and flanking sequences are treated with exonuclease III (ExoIII) which removes nucleotides from the ends of DNA molecules at a fixed rate. Reaction conditions are set such that DNA molecules are recovered with progressive 1 base pair deletions in the flanking sequences after ExoIII digestion. Treatment of the individual cis-acting sequence element DNA molecules with ExoIII before adding them in random ligation reaction to form the combined transcription regulatory elements results in increased randomness of the spacing between the cis-acting sequence elements in the combined promoter cassette.

In cases of several developmentally regulated transcription factors, the specificity of cis-acting sequence elements varies depending on the members of the family. In such cases and when the exact consensus cis-acting sequences for transcription factors are not clearly known or when they must be determined, cell type-specific sequences of the relevant target elements are determined experimentally. The CASTing (cyclic amplification and selection of targets) protocol has been used for detecting cis-acting sequences of transcription factors, especially for multicomponent complexes (14). In the protocol, an aliquot of double stranded oligonucleotides containing a stretch of degenerate random nucleotides (15–35 bp) in the middle is mixed with a nuclear extract prepared from the target cells. Protein-DNA complexes are immunoprecipitated using an antibody specific to the particular transcription factor, bound DNA molecules are PCR amplified, and used again for another cycle of nuclear protein binding and immunoprecipitation. Several repeated cycles enrich the population of random oligonucleotides only for the ones with the highest binding affinity to the transcription factor. From the resulting high affinity nucleotide sequences a consensus binding sequence is deduced. Therefore, cis-acting sequences determined for particular transcription factors using this method may more accurately reflect the binding preferences of the proteins in vivo in the presence of other interacting regulators and co-regulators. Carefully determining the sequences for the oligonucleotides for cis-acting elements using these methods before adding them in the random ligation reactions increases the likelihood of producing optimal promoter cassettes.

Example 2.1

Experimental Procedures

Example 2.1.1

CASTing for Cis-Acting Sequence Determination

CASTing is done for transcription factors requiring exact binding sequences in the context of other interacting regulators and co-regulators. CASTing is performed essentially in the same manner as disclosed in Funk et al (14) and Wright et al (58), with minor modifications. The contents of Funk et al and Wright et al are incorporated by reference herein in their entirety especially as they related to methods of determining cis-acting sequences. An oligonucleotide is made with about 25 random nucleotide sequence in the middle and with three different restriction sites at each end (Sal I-Hind III-Xba I-N25-EcoRI-BamHI-Xho I). About 25 bp sequences at both ends containing restriction sites and spacer nucleotides are used for designing forward and reverse primers for PCR amplification. The oligonucleotides are made double stranded by extension with Taq DNA polymerase for 30 min using the reverse primer as the sole PCR primer. A sample of this double stranded oligonucleotide is mixed with a nuclear extract prepared from SK-N-BE(2)-C cells in a final concentration of NaCl at approximately 100 mM, and in the presence of 10 μg of sonicated salmon sperm DNA to decrease non-specific interactions. Protein-DNA complex is immunoprecipitated using magnetic beads (Dynal Inc., Great Neck, N.Y.) coated with an antibody raised against the target transcription factor. The protein-DNA-bead complex is recovered using a magnet and washed three times with PBS containing 0.5% NP-40 and 0.1% BSA. The complex is resuspended in 30 μl of PCR reaction buffer and is amplified using the forward and reverse primers for 9 cycles (5 min at 100° C. to denature, followed by addition of Taq and 9 cycles of 94° C. 1 min, 65° C. 1 min, and 72° C. 1 min with 10 min of extension). A 10 μl amplified sample is used again in another cycle of CASTing. Six CASTing cycles are performed and resulting DNA samples are cloned into a plasmid and approximately 30 different clones are picked, sequenced, and a consensus sequence is deduced.

Example 2.1.2

Random Ligation of Cis-Acting Sequence Oligonucleotides

A set of complementary oligonucleotides is synthesized to contain a specific cis-acting sequence element and the flanking sequences for each of the transcription factors selected after the analysis of TREP profiling DNA microarray assay results. Each set of complementary oligonucleotides is annealed and phosphorylated in one reaction in TEN buffer (10 mM Tris-HCl, pH 7.5; 1 mM EDTA; 50 mM NaCl). The reaction is carried out in a final volume of 300 µl, containing 20 µM of each of the complementary oligonucleotides, 1 mM ATP, and 0.5 U/ml of T4 polynucleotide kinase, for 15 min at 70° C., and slowly cooled to room temperature over a 30 min period. For the random ligation reaction, the same molar amount of oligonucleotides for different cis-acting sequences are used in maintaining the total amount of oligonucleotide of 200 pmol in a final reaction volume of 150 µl. Ligation is done using 20 U of T4 DNA ligase at 16° C. overnight. The ligation mixture is run on a 6% acrylamide gel, and a portion of the gel containing DNA bands between 75 bp to 1.0 kb is cut. DNA fragments are eluted from the gel piece using Qiaex II Gel Extraction kit (Qiagen, Chatsworth, Calif.), after incubating the gel piece in two volumes of diffusion buffer at 37° C. overnight. Purified DNA fragments are incubated in a 150 µl of ligation reaction containing a phosphorylated and annealed 12 bp complementary oligonucleotides containing a 8 bp Asc I restriction site in the middle, with 10 U of T4 ligase at 16° C. overnight. The reaction is cleaned up using Qiaquick Nucleotide Removal kit (Qiagen), digested with Asc I, and ligated into the Asc I site of the β-galactosidae reporter plasmid (pD96L). As shown in FIG. 1, in pD96L, β-galactosidase reporter gene is placed downstream of the dopamine β-hydroxylase (DBH) minimum promoter containing 45 bp of promoter sequence with TATA-box as well as 51 bp of 5' untranslated region of the gene. The ligated clones are purified by Qiaquick Nucleotide Removal kit and transformed into electrocompetent *E coli* DH10b strain. Transformed bacterial cells are seeded as one batch into 5 ml LB in the presence of ampicillin (100 µg/ml) for 8 hours and are amplified into 200 ml overnight. Plasmids are isolated using Qiagen Maxi prep.

Example 3

Pre-Screening the Library Using FACS for the Selection of Best Performing Sequence Combinations Target SK-N-BE(2)-C neuroblastoma cells are transfected with a library of plasmids containing randomly combined promoter cassettes cloned upstream of the LacZ gene. FACS is used to select approximately 3–5% of transfected cells with strong β-galactosidase expression. Plasmids are isolated from sorted cells, amplified and used again in transfection of SK-N-BE(2)-C cells. The same procedure is repeated three to four times so that the resulting cell population contains plasmids capable of expressing reporter gene at the highest level. After the final sorting, plasmids are isolated and amplified individually and are used in 96-well transient transfection assays. SK-N-BE(2)-C cells are chosen for pre-screening as these cells have the highest potential for metastasis and thus are the primary target in gene therapy for advanced-stage neuroblastoma. These cells also grow aggressively in culture, and a relatively high level of transfection efficiency can be achieved in these cells. Up to 90% of transfection efficiency can be achieved in SK-N-BE(2)-C cells using Metafectene reagent (Biontex; Munich, Germany).

Example 3.1

Experimental Procedure

Example 3.1.1

Transfection of SK-N-BE(2)-C Cells and Sorting by FACS

SK-N-BE(2)-C neuroblastoma cells are grown in D-10 in T75 flasks. Approximately $1 \times 10^7$ of SK-N-BE(2)-C cells are transfected with 20 µg of plasmid DNA library and 50 µl of Metafectene according to the manufacturer's protocol. Forty-eight hours after transfection, cells are detached from the culture plate using 5 mM EDTA in PBS and passed through a 23-gauge needle to further dissociate doublets and clumps. Cells are resuspended in 0.2 ml of PBS, transferred to a Falcon 2085 tube and warmed to 37° C. Flow cytometry analysis of β-Gal activity of the cells is performed as described in Fiering et al (12), Huang et al (20), and Nolan et al (44), which are incorporated by reference in their entirety, especially as they relate to flow cytometry techniques. Briefly, 200 µl of 2 mM fluorescein di-β-D-galactoside (FDG; Molecular Probes) in $H_2O$ is added to the cells, and the mixture is incubated at 37° C. for 1 min. At the end of the incubation, 10 volumes of ice-cold PBS are added and cells are kept on ice for 20–60 min. The reaction is terminated by adding 2 mM phenylethyl-β-D-thiogalactoside (Molecular Probes). Prior to sorting, propodium iodide (Sigma) is added at 5 µg/ml. Cells are sorted at 4° C. on a FACS machine. Fluorescein isothiocyanate (FITC)-positive cells at the upper 3–5% level are collected from the sorter.

Example 3.1.2

Recovery of Plasmids from Sorted Cells

Plasmids in the sorted cells are extracted by the Hirt protocol (19) which was developed to extract low molecular weight DNA through the preferential precipitation of cellular genomic DNA in the presence of SDS and NaCl. Briefly, sorted cells are suspended in 45 mM Tris-borate, 1 mM EDTA. 0.5% SDS and 1.6 M sodium chloride and digested at 4° C. overnight. The cellular extract is pelleted and DNA is extracted from the supernatant two times with phenol/chloroform/isoamylalcohol (25:24:1) and once with chloroform. DNA is precipitated with ethanol and resuspended in 50 µl of $H_2O$. The plasmid DNA isolated from sorted cells is then used for transforming highly efficient electro-competent *E coli* DH10b strain, grown as a mixed culture overnight in 200 ml LB supplemented with ampicillin. The plasmids are isolated using a Qiagen Maxi kit.

Example 3.1.3

Repeated Sorting

The same cycle of transfection, sorting and plasmid DNA isolation, are performed three to four times so that the majority of clones with low to intermediate level of reporter gene expression are eliminated. Sequence combinations driving reporter gene expression at the highest level survive the progressive selection process. After the final round of the selection, plasmids are isolated from the sorted cells, transformed in *E. coli* and plated on an agar plate (with 100 µg/ml ampicillin). From the plate, 90–100 bacterial transformants are picked, cultured overnight and used for plasmid preps individually. The threshold of selection (3–5%) during FACS cell sorting for each cycle and the number of cycles (3–4) are optimized empirically so that after the final round, approximately 90–100 best performing sequence combinations survive the selection process. Selected plasmids are sequenced and used in the additional screening procedure.

Example 4

Screen Pre-Selected Combinations in 96-Well Transient Transfection Assays in Both Target and Non-Target Cells for a Final Selection of the 3–5 Best-Performing Candidates In this procedure, about 90 different combined promoter cassettes pre-selected in terms of their performance in SK-N-BE(2)-C cells analyzed by FACS are individually tested in transient transfection assays in SK-N-BE(2)-C cells, in SH-SY5Y and SH-EP1 cells, and other non-target cells. Performance of each combined transcription regulatory element in target cells as well as in non-target cells are scored, and the 3–5 best scoring combinations are selected for further analysis. The scoring criteria are the efficiency of transcription in target cells and the absence of transcriptional activity in non-target cells. The assay is performed in various different non-target cells including without limitation HeLa cells, HCN-LA and HCN-2 human cortical neuronal cells (ATCC, Manassas, Va.), HNPC human neuronal precursor cells (Clonexpress, Inc., Gaithersburg, Md.), ARPE-19 human retinal pigment epithelia cells (ATCC), 293 human kidney cells (ATCC), HepG2 human hepatocellular carcinoma cells, and other non-human cells such as PC12 and NIH 3T3.

Example 4.1

Experimental Procedures

For transient transfection assays, 10,000 to 30,000 cells are plated on duplicate 96-well plates in an appropriate growth media 12–16 hours before transfection. The plating density is determined so that cells become 70–90% confluent at the time of transfection. Cells are also pre-tested for transfection efficiency using different commercially available transfection reagents including Metafectene, Lifofectamine (Invitrogen), Fugene-6 (Roche), and Superfectene (Qiagen). Cells are transfected with an appropriate transfection reagent following manufacturer's protocol using 50–200 ng of DNA. Cells are then washed with PBS and lysed 48 hrs after transfection using 50 µl of the reporter lysis buffer (Promega) and assayed directly on the plate for β-Gal activity using a β-galactosidase assay system (Promega). In addition to the about 90 pre-selected plasmid DNA samples, CMV enhancer/promoter-driven β-Gal reporter plasmid and the reporter plasmid, driven by the minimum DBH promoter, are added in duplicates as positive and negative controls, respectively. Also, 522 bp tyrosine hydroxylase promoter (50) driven β-Gal reporter plasmid is used in duplicate wells as a control for cell type-specificity. As different cell types show varying transcription efficiency, β-Gal activities recorded from different cells using the same plasmid clone are not directly comparable for scoring. So, the performance of plasmid samples with different cis-acting sequence combinations are expressed as a percent against the value obtained from CMV enhancer/promoter-driven positive control wells after subtracting the background signal obtained from the negative control wells. The best scoring 3–5 plasmids in terms of the strength of expression in target cells and the absence of expression in non-target cells are chosen.

REFERENCES

1. Ahmad, I., H. R. Acharya, J. A. Rogers, A. Shibata, T. E. Smithgall, and C. M. Dooley. 1998. The role of NeuroD as a differentiation factor in the mammalian retina. J Mol Neurosci 11:165–78.

2. Berman, H. M., T. Battistuz, T. N. Bhat, W. F. Bluhm, P. E. Bourne, K. Burkhardt, Z. Feng, G. L. Gilliland, L. Iype, S. Jain, P. Fagan, J. Marvin, D. Padilla, V. Ravichandran, B. Schneider, N. Thanki, H. Weissig, J. D. Westbrook, and C. Zardecki. 2002. The Protein Data Bank. Acta Crystallogr D Biol Crystallogr 58:899–907.

3. Brandeis, M., D. Frank, I. Keshet, Z. Siegfried, M. Mendelsohn, A. Nemes, V. Temper, A. Razin, and H. Cedar. 1994. Sp1 elements protect a CpG island from de novo methylation. Nature 371:435–8.

4. Brunet, J. F., and A. Pattyn. 2002. Phox2 genes-from patterning to connectivity. Curr Opin Genet Dev 12:435–40.

5. Bushman, F. 1995. Targeting retroviral integration. Science 267:1443–4.

6. Collingwood, T. N., F. D. Urnov, V. K. Chatterjee, and A. P. Wolffe. 2001. Chromatin remodeling by the thyroid hormone receptor in regulation of the thyroid-stimulating hormone alpha-subunit promoter. J Biol Chem 276:34227–34.

7. Costa, R. H., V. V. Kalinichenko, A. X. Holterman, and X. Wang. 2003. Transcription factors in liver development, differentiation, and regeneration. Hepatology 38:1331–47.

8. Deroo, B. J., and T. K. Archer. 2001. Glucocorticoid receptor-mediated chromatin remodeling in vivo. Oncogene 20:3039–46.

9. Dobbelstein, M. 2004. Replicating adenoviruses in cancer therapy. Curr Top Microbiol Immunol 273:291–334.

10. Dubreuil, V., M. R. Hirsch, A. Pattyn, J. F. Brunet, and C. Goridis. 2000. The Phox2b transcription factor coordinately regulates neuronal cell cycle exit and identity. Development 127:5191–201.

11. Engler, S., C. Thiel, K. Forster, K. David, R. Bredehorst, and H. Juhl. 2001. A novel metastatic animal model reflecting the clinical appearance of human neuroblastoma: growth arrest of orthotopic tumors by natural, cytotoxic human immunoglobulin M antibodies. Cancer Res 61:2968–73.

12. Fiering, S. N., M. Roederer, G. P. Nolan, D. R. Micklem, D. R. Parks, and L. A. Herzenberg. 1991. Improved FACS-Gal: flow cytometric analysis and sorting of viable eukaryotic cells expressing reporter gene constructs. Cytometry 12:291–301.

13. Fry, C. J., and C. L. Peterson. 2001. Chromatin remodeling enzymes: who's on first? Curr Biol 11:R185–97.

14. Funk, W. D., and W. E. Wright. 1992. Cyclic amplification and selection of targets for multicomponent complexes: myogenin interacts with factors recognizing binding sites for basic helix-loop-helix, nuclear factor 1, myocyte-specific enhancer-binding factor 2, and COMP1 factor. Proc Natl Acad Sci USA 89:9484–8.

15. Gaston, K., and P. S. Jayaraman. 2003. Transcriptional repression in eukaryotes: repressors and repression mechanisms. Cell Mol Life Sci 60:721–41.

16. Hahm, S. H., and L. E. Eiden. 1998. Cis-regulatory elements controlling basal and inducible VIP gene transcription. Ann N Y Acad Sci 865:10–26.

17. Hamm, A., N. Krott, I. Breibach, R. Blindt, and A. K. Bosserhoff. 2002. Efficient transfection method for primary cells. Tissue Eng 8:235–45.

18. Haviv, Y. S., and D. T. Curiel. 2001. Conditional gene targeting for cancer gene therapy. Adv Drug Deliv Rev 53:135–54.

19. Hirt, B. 1967. Selective extraction of polyoma DNA from infected mouse cell cultures. J Mol Biol 26:365–9.

20. Huang, J., T. K. Blackwell, L. Kedes, and H. Weintraub. 1996. Differences between MyoD DNA binding and activation site requirements revealed by functional random sequence selection. Mol Cell Biol 16:3893–900.

21. Hwang, D. Y., W. A. Carlezon, Jr., O. Isacson, and K. S. Kim. 2001. A high-efficiency synthetic promoter that drives transgene expression selectively in noradrenergic neurons. Hum Gene Ther 12:1731–40.

22. Irving, J., Z. Wang, S. Powell, C. O'Sullivan, M. Mok, B. Murphy, L. Cardoza, J. S. Lebkowski, and A. S. Majumdar. 2004. Conditionally replicative adenovirus driven by the human telomerase promoter provides broad-spectrum antitumor activity without liver toxicity. Cancer Gene Ther 11:174–85.

23. Janknecht, R. 2004. On the road to immortality: hTERT upregulation in cancer cells. FEBS Lett 564:9–13.

24. Kasahara, N., A. M. Dozy, and Y. W. Kan. 1994. Tissue-specific targeting of retroviral vectors through ligand-receptor interactions. Science 266:1373–6.

25. Kawashima, T., S. Kagawa, N. Kobayashi, Y. Shirakiya, T. Umeoka, F. Teraishi, M. Taki, S. Kyo, N. Tanaka, and T. Fujiwara. 2004. Telomerase-specific replication-selective virotherapy for human cancer. Clin Cancer Res 10:285–92.

26. Keith, W. N., and S. F. Hoare. 2004. Detection of telomerase hTERT gene expression and its splice variants by RT-PCR. Methods Mol Med 97:297–309.

27. Kim, H. S., H. Seo, C. Yang, J. F. Brunet, and K. S. Kim. 1998. Noradrenergic-specific transcription of the dopamine beta-hydroxylase gene requires synergy of multiple cis-acting elements including at least two Phox2a-binding sites. J Neurosci 18:8247–60.

28. Koeneman, K. S., and J. T. Hsieh. 2001. The prospect of gene therapy for prostate cancer: update on theory and status. Curr Opin Urol 11:489–94.

29. Kumar, R., and E. B. Thompson. 2003. Transactivation functions of the N-terminal domains of nuclear hormone receptors: protein folding and coactivator interactions. Mol Endocrinol 17:1–10.

30. Kumer, S. C., and K. E. Vrana. 1996. Intricate regulation of tyrosine hydroxylase activity and gene expression. J Neurochem 67:443–62.

31. Lang, D., and J. A. Epstein. 2003. Sox10 and Pax3 physically interact to mediate activation of a conserved c-RET enhancer. Hum Mol Genet 12:937–45.

32. Lanson, N. A., Jr., P. L. Friedlander, P. Schwarzenberger, J. K. Kolls, and G. Wang. 2003. Replication of an adenoviral vector controlled by the human telomerase reverse transcriptase promoter causes tumor-selective tumor lysis. Cancer Res 63:7936–41.

33. Lastowska, M., C. Cullinane, S. Variend, S. Cotterill, N. Bown, S. O'Neill, K. Mazzocco, P. Roberts, J. Nicholson, C. Ellershaw, A. D. Pearson, and M. S. Jackson. 2001. Comprehensive genetic and histopathologic study reveals three types of neuroblastoma tumors. J Clin Oncol 19:3080–90.

34. Lee, J. E., S. M. Hollenberg, L. Snider, D. L. Turner, N. Lipnick, and H. Weintraub. 1995. Conversion of *Xenopus* ectoderm into neurons by NeuroD, a basic helix-loop-helix protein. Science 268:836–44.

35. Lemon, B., and R. Tjian. 2000. Orchestrated response: a symphony of transcription factors for gene control. Genes Dev 14:2551–69.

36. Li, X., E. M. Eastman, R. J. Schwartz, and R. Draghia-Akli. 1999. Synthetic muscle promoters: activities exceeding naturally occurring regulatory sequences. Nat Biotechnol 17:241–5.

37. Liu, J., A. Baykal, K. M. Fung, J. A. Thompson-Lanza, A. Hoque, S. M. Lippman, and A. Sahin. 2004. Human telomerase reverse transcriptase mRNA is highly expressed in normal breast tissues and down-regulated in ductal carcinoma in situ. Int J Oncol 24:879–84.

38. Liu, K., M. M. Schoonmaker, B. L. Levine, C. H. June, R. J. Hodes, and N. P. Weng. 1999. Constitutive and regulated expression of telomerase reverse transcriptase (hTERT) in human lymphocytes. Proc Natl Acad Sci USA 96:5147–52.

39. Lou, E. 2003. Oncolytic herpes viruses as a potential mechanism for cancer therapy. Acta Oncol 42:660–71.

40. Machon, O., V. Strmen, J. Hejnar, J. Geryk, and J. Svoboda. 1998. Sp1 binding sites inserted into the rous sarcoma virus long terminal repeat enhance LTR-driven gene expression. Gene 208:73–82.

41. Macleod, D., J. Charlton, J. Mullins, and A. P. Bird. 1994. Sp1 sites in the mouse aprt gene promoter are required to prevent methylation of the CpG island. Genes Dev 8:2282–92.

42. Matthay, K. K., J. G. Villablanca, R. C. Seeger, D. O. Stram, R. E. Harris, N. K. Ramsay, P. Swift, H. Shimada, C. T. Black, G. M. Brodeur, R. B. Gerbing, and C. P. Reynolds. 1999. Treatment of high-risk neuroblastoma with intensive chemotherapy, radiotherapy, autologous bone marrow transplantation, and 13-cis-retinoic acid. Children's Cancer Group. N Engl J Med 341:1165–73.

43. Nettelbeck, D. M., V. Jerome, and R. Muller. 2000. Gene therapy: designer promoters for tumour targeting. Trends Genet 16:174–81.

44. Nolan, G. P., S. Fiering, J. F. Nicolas, and L. A. Herzenberg. 1988. Fluorescence-activated cell analysis and sorting of viable mammalian cells based on beta-D-galactosidase activity after transduction of *Escherichia coli* lacZ. Proc Natl Acad Sci USA 85:2603–7.

45. Okuwaki, M., A. Iwamatsu, M. Tsujimoto, and K. Nagata. 2001. Identification of nucleophosmin/B23, an acidic nucleolar protein, as a stimulatory factor for in vitro replication of adenovirus DNA complexed with viral basic core proteins. J Mol Biol 311:41–55.

46. Pattyn, A., C. Goridis, and J. F. Brunet. 2000. Specification of the central noradrenergic phenotype by the homeobox gene Phox2b. Mol Cell Neurosci 15:235–43.

47. Post, D. E., F. R. Khuri, J. W. Simons, and E. G. Van Meir. 2003. Replicative oncolytic adenoviruses in multimodal cancer regimens. Hum Gene Ther 14:933–46.

48. Reynolds, P. N., S. A. Nicklin, L. Kaliberova, B. G. Boatman, W. E. Grizzle, I. V. Balyasnikova, A. H. Baker, S. M. Danilov, and D. T. Curiel. 2001. Combined transductional and transcriptional targeting improves the specificity of transgene expression in vivo. Nat Biotechnol 19:838–42.

49. Ross, R. A., J. L. Biedler, and B. A. Spengler. 2003. A role for distinct cell types in determining malignancy in human neuroblastoma cell lines and tumors. Cancer Lett 197:35–9.

50. Steffens, S., A. Sandquist, S. Frank, U. Fischer, C. Lex, N. G. Rainov, and C. M. Kramm. 2004. A Neuroblastoma-Selective Suicide Gene Therapy Approach Using the Tyrosine Hydroxylase Promoter. Pediatr Res 56:268–277.

51. Stein, G. S., J. B. Lian, J. L. Stein, and A. J. van Wijnen. 2000. Bone tissue specific transcriptional control: options for targeting gene therapy to the skeleton. Cancer 88:2899–902.

52. Uchiyama, K., R. Otsuka, and K. Hanaoka. 1999. CHox11L2, a Hox11 related gene, is expressed in the peripheral nervous system and subpopulation of the spinal cord during chick development. Neurosci Lett 273:97–100.

53. Urnov, F. D., and A. P. Wolffe. 2001. Chromatin remodeling and transcriptional activation: the cast (in order of appearance). Oncogene 20:2991–3006.

54. Weinstein, J. L., H. M. Katzenstein, and S. L. Cohn. 2003. Advances in the diagnosis and treatment of neuroblastoma. Oncologist 8:278–92.

55. West, A. E., W. G. Chen, M. B. Dalva, R. E. Dolmetsch, J. M. Kornhauser, A. J. Shaywitz, M. A. Takasu, X. Tao, and M. E. Greenberg. 2001. Calcium regulation of neuronal gene expression. Proc Natl Acad Sci USA 98:11024–31.

56. Wildner, O. 2003. Comparison of replication-selective, oncolytic viruses for the treatment of human cancers. Curr Opin Mol Ther 5:351–61.

57. Wilson, M., and P. Koopman. 2002. Matching SOX: partner proteins and co-factors of the SOX family of transcriptional regulators. Curr Opin Genet Dev 12:441–6.

58. Wright, W. E., M. Binder, and W. Funk. 1991. Cyclic amplification and selection of targets (CASTing) for the myogenin consensus binding site. Mol Cell Biol 11:4104–10.

59. Yang, C., H. S. Kim, H. Seo, C. H. Kim, J. F. Brunet, and K. S. Kim. 1998. Paired-like homeodomain proteins, Phox2a and Phox2b, are responsible for noradrenergic cell-specific transcription of the dopamine beta-hydroxylase gene. J Neurochem 71:1813–26.

60. You, L., B. He, Z. Xu, F. McCormick, and D. M. Jablons. 2004. Future directions: oncolytic viruses. Clin Lung Cancer 5:226–30.

61. Zou, W., C. Luo, Z. Zhang, J. Liu, J. Gu, Z. Pei, C. Qian, and X. Liu. 2004. A novel oncolytic adenovirus targeting to telomerase activity in tumor cells with potent. Oncogene 23:457–64.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method for making and selecting a transcription enhancing combined promoter cassette comprising:
   (i) constructing a library of randomly combined transcription regulatory elements, each of which comprises double stranded DNA sequence elements that are recognized by a specific transcription regulator and flanking sequences;
   (ii) inserting the combined transcription regulatory elements upstream of a minimum promoter followed by a reporter gene in a vector;
   (iii) inserting the vector into a host cell; and
   (iv) screening for the cells showing enhanced expression of the reporter gene, and identifying the combined promoter cassette in the cell, wherein the DNA sequence elements that are recognized by transcription regulators are obtained by DNA microarray profiling of transcription regulators and co-regulators.

2. The method according to claim 1, wherein the library of randomly combined transcription regulatory elements is made by mixing individual double stranded DNA sequence elements that are recognized by transcription regulators together under ligation reaction conditions.

3. The method according to claim 1, wherein the double stranded DNA sequence element comprises spacer nucleotides at either or both ends.

4. The method according to claim 1, wherein the reporter gene expression is screened by fluorescence-activated cell sorter (FACS).

5. The method according to claim 1, wherein the reporter gene is lacZ or GFP.

6. The method according to claim 1, wherein the host cell is cancer cell.

7. The method according to claim 6, wherein the cancer is neuroblastoma.

8. A method for making and selecting a transcription enhancing combined promoter cassette comprising:
   (i) constructing a library of randomly combined transcription regulatory elements, each of which comprises double stranded DNA sequence elements that are recognized by a specific transcription regulator and flanking sequences;
   (ii) inserting the combined transcription regulatory elements upstream of a minimum promoter followed by a reporter gene in a vector;
   (iii) inserting the vector into a neuroblastoma host cell; and
   (iv) screening for the cells showing enhanced expression of the reporter gene, and identifying the combined promoter cassette in the cell.

9. The method according to claim 8, wherein the librazy of randomly combined transcription regulatory elements is made by mixing individual double stranded DNA sequence elements that are recognized by transcription regulators together under ligation reaction conditions.

10. The method according to claim 8, wherein the double stranded DNA sequence element comprises spacer nucleotides at either or both ends.

11. The method according to claim 8, wherein the reporter gene expression is screened by fluorescence-activated cell sorter (FACS).

12. The method according to claim 8, wherein the reporter gene is lacZ or GFP.

* * * * *